United States Patent
Bartic et al.

(10) Patent No.: US 6,521,109 B1
(45) Date of Patent: Feb. 18, 2003

(54) DEVICE FOR DETECTING AN ANALYTE IN A SAMPLE BASED ON ORGANIC MATERIALS

(75) Inventors: Carmen Bartic, Iasi (RO); Jef Poortmans, Leuven (BE); Kris Baert, Leuven (BE)

(73) Assignee: Interuniversitair Microelektronica Centrum (IMEC) vzw, Leuven (BE)

( * ) Notice: Subject to any disclaimer, the term of this patent is extended or adjusted under 35 U.S.C. 154(b) by 0 days.

(21) Appl. No.: 09/660,763

(22) Filed: Sep. 13, 2000

Related U.S. Application Data (60) Provisional application No. 60/154,426, filed on Sep. 17, 1999.

(30) Foreign Application Priority Data

Sep. 13, 1999 (EP) .............................................. 99870186

(51) Int. Cl.[7] .............................................. G01N 27/414
(52) U.S. Cl. .................................. 204/403.01; 204/416
(58) Field of Search .............................. 204/403, 412, 204/416, 433, 418, 419

(56) References Cited

U.S. PATENT DOCUMENTS

| | | | | |
|---|---|---|---|---|
| 4,084,173 A | * | 4/1978 | Fantechi | 357/42 |
| 4,322,680 A | | 3/1982 | Janata et al. | 324/71.2 |
| 5,543,024 A | * | 8/1996 | Hanazato et al. | 204/403 |
| 6,060,338 A | * | 5/2000 | Tanaka et al. | 438/99 |
| 6,153,070 A | * | 11/2000 | Maurer et al. | 204/416 |
| 6,291,088 B1 | * | 9/2001 | Wong et al. | 428/698 |

FOREIGN PATENT DOCUMENTS

| | | |
|---|---|---|
| DE | 4427 921 A1 | 2/1996 |
| EP | 0 241 991 A2 | 10/1987 |
| EP | 0 258 951 A2 | 3/1988 |
| EP | 0 395 136 A2 | 10/1990 |
| EP | 0 821 228 A1 | 1/1998 |
| JP | 404254750 A | * 9/1992 |
| JP | 405312746 A | * 11/1993 |
| JP | 410260156 A | * 9/1998 |
| WO | WO 87/00633 | 1/1987 |
| WO | WO 99/10939 | 3/1999 |

OTHER PUBLICATIONS

JAPIO abstract of Wada et al. (JP410260156A).*
JAPIO abstract of Enmanji et al. (JP405312746A).*
JAPIO abstract of Sohn et al. (JP404254750A).*
Partial printout of ACS–Registry data sheet for compound RN No. 26498–02–2.*
Garner, F. et al.; "*All–Polymer Field–Effect Transistor Realized by Printing Techniques*"; Science, US., American Association for the Advancement fo Science; vol. 265; Sep. 16, 1994; pp. 1684–1686.
Garner, F. et al.; "*An All–Organic Soft Thin Film Transistor with Very High Carrier Mobility*"; Advanced Materials; vol. 2, No. 12, 1990; pp. 592–594.
European Search Report; Application No. EP 99 87 0186.

(List continued on next page.)

*Primary Examiner*—Jill Warden
*Assistant Examiner*—Alex Noguerola
(74) *Attorney, Agent, or Firm*—Knobbe, Martens, Olson & Bear LLP

(57) ABSTRACT

A device for detecting an analyte in a sample comprising an active layer comprising at least a dielectric material, a source electrode, a drain electrode and a semiconducting substrate which acts as current pathway between source and drain. The conductivity of said semiconducting layer can be influenced by the interaction of the active layer with the sample containing the analyte to detect. The device is fabricated such that properties like low price, disposability, reduced drift of the device and suitability for biomedical and pharmaceutical applications are obtained. To fulfill these requirements, the device described in this application will be based on organic-containing materials.

27 Claims, 4 Drawing Sheets

OTHER PUBLICATIONS

P. Bergveld; "*Development of an Ion–Sensitive Solid–State Device for Neurophysiologial Measurements*"; IEEE Trans. Biomed. Eng., BME–17, 1970, pp. 70–71 Jan.

C. D. Fung et al.; "*A Generalized Theory of an Eletrolyte––Insulator Semiconductor Field–Effect Transistor*"; IEEE Trans. El. Dev., vol. ED–33, No. 1, 1986, pp. 8–18 Month unknown.

Garnier et al.; "*All Polymer field–Effect transistor Realized by Printing Tchniques*"; Science, 1994, vol. 265, pp. 1684–1686 Sep.

G. Harsanyi; "*Polymer Films in Sensor Applications—Technology, Materials, Devices and Their Characteristics*"; Technomic Publishing Co. Inc., Lancaster–Basel, 1995, pp 53–92 and pp 149–155, and. p. 2 Month unknown.

G. Bidan, "*Electroconducting conjugated polymers; new sensitive matrices to build up chemical or electrochemical sensors*", Sensors and Actuators B, vol. 6, 1992, pp. 45–56.

H.H. van den Vlekkert et al.; "*a pH–isfet and Integrated pH–pressure Sensor with Back–Side Contacts*"; Proc. $2^{nd}$ Int. Meeting on Chemical Sensors, Bordeaux, France, 1986; pp. 462 Month unknown.

W. Gopel, et al.; *Sensors* "*A Comprehensive Survey*"; vol. 2, Part 1, 1991, pp 467–528 Month unknown.

\* cited by examiner

Figure 1

PRIOR ART

Step 1

Step 2

Step 3

Step 4

DEVICE FOR DETECTING AN ANALYTE IN A SAMPLE BASED ON ORGANIC MATERIALS

RELATED APPLICATION

The present application claims the priority of U.S. provisional patent application Ser. No. 60/154,426 filed Sep. 17, 1999.

FIELD OF THE INVENTION

The present invention relates to a device for detecting an analyte in a sample belonging to a class of devices known as chemically-sensitive field-effect transistors (CHEMFET's) which are of particular interest for biomedical and industrial applications.

BACKGROUND OF THE INVENTION

There is considerable interest in methods for detection, measuring and monitoring chemical properties of a sample. A sample can be a solid, solution, gas, vapor or a mixture of those. The chemical properties of the sample are determined by the analyte present in the sample, the analyte can be e.g. an electrolyte, a biomolecule or a neutral molecule.

Chemical sensors belonging to a class of devices known as Chemically Sensitive Field-Effect Transistors (CHEMFET's) are of particular interest for biomedical and industrial applications. Chemically sensitive field-effect transistors measure chemical properties of the samples to which the device is exposed. In a CHEMFET, the changes at the surface of the gate dielectric are detected via the modulations of the electric field in the channel of a field-effect transistor. Such chemical changes can be induced by e.g. the presence of ions in aqueous solutions, but also by the interaction of an electroinactive organic compound with a biological-sensing element in contact with the gate of the field-effect transistor. In this way, the concentration of ions or organic biomolecules (e.g. glucose, cholesterol, and the like) in aqueous solutions can be measured. One promising application of this type of device regards the monitoring of the cell metabolism for fundamental research or drug-characterization studies.

Figure 1:
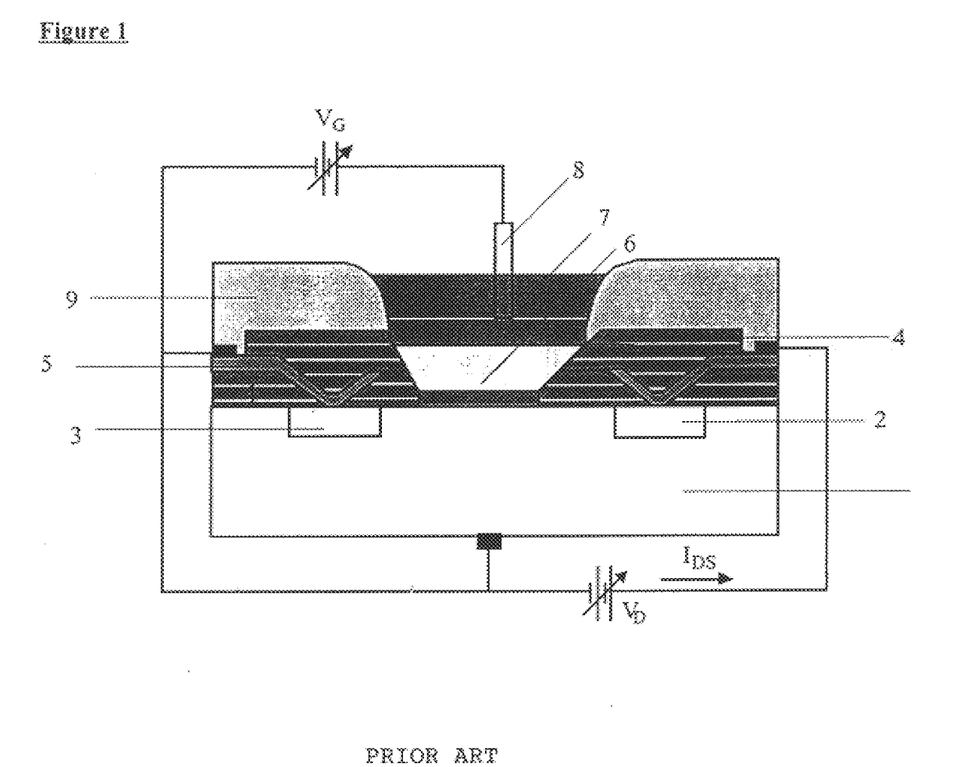
FIG. 1 illustrates an ion-sensitive field-effect transistor (ISFET) fabricated with CMOS technology (H. H. van den Vlekkert et. al., *Proc. 2nd Int. Meeting on Chemical Sensors, Bordeaux,* France, 1986,pp. 462.)

Among CHEMFET devices, the ion-sensitive field-effect transistors are best known. The concept of ion-sensitive field-effect transistor (ISFET) has been introduced by P. Bergveld in 1970 [P. Bergveld, *IEEE Trans. Biomed. Eng.*, BME-17, 1970, pp. 70]. It was demonstrated that when the metal gate of an ordinary MOSFET is omitted and the dielectric layer is exposed to an electrolyte, the characteristics of the transistor are affected by the ionic activity of the electrolyte. The schematic drawing of a classic ISFET is shown in FIG. 1. The silicon substrate 1 of the device acts as current pathway between the source region 3 and the drain region 2. Both regions are contacted by metal electrodes 5. The dielectric layer 4 is covered with an ion-selective membrane 6 which is exposed to the solution 7. The device is encapsulated with an encapsulating material 9. Optionally, a reference electrode 8 can be present.

ISFET's have first been developed for pH and $Na^+$ activity detection in aqueous solutions (C. D. Fung, P. W. Cheung and W. H. Ko, *IEEE Trans. El. Dev.*, Vol. ED-33, No.1, 1986, pp.8–18). The cation-sensitivity of the device is determined by the ionization and complexation of the surface hydroxyl groups on the gate dielectric surface. ISFET devices for $Ca^{2+}$, $K^+$ activity monitoring have also been fabricated. The sensitivity towards these ions is achieved by incorporating a sensitized plastic membrane (PVC) in contact with the gate dielectric. Therefore, these sensors detect changes in the charge of the membrane or in the transmembranar potential. Besides the use of CHEMFET devices for the determination of ions (ISFET), CHEMFET's have also been employed as enzyme-sensitive FET (ENFET's) for organic molecule detection or immuno-sensitive FET's (IMFET's) for immunochemicals (antigen, antibody) monitoring.

CHEMFET's exhibit important advantages over conventional chemically selective electrodes. Usually, CHEMFET's are fabricated with standard CMOS technology, which offers the advantages of miniaturization and mass production. In the biomedical field, there is an especially important area for the application of miniaturized sensors. The sensor is mounted in the tip of indwelling catheters, through which their feasibility for monitoring blood electrolytes and parameters has been demonstrated.

The fabrication method offers the additional benefit of the fabrication of multi-ion sensors and integration in smart sensors and sensor arrays. A further advantage of the use of CHEMFET is the logarithmic response of the potential in function of the analyte concentration. This type of response is interesting if a broad concentration range is investigated. Since the response of a CHEMFET device is initiated by the field-effect, this response is very fast compared to the response of conventional chemically sensitive electrodes. Up to now, all CHEMFET devices are based on silicon or silicon based materials.

However, there are some problems that so far have hampered the commercial applications of these devices. The most important problem of the CHEMFET is the drift of the device. Drift is typically characterized by a relatively slow, monotonic temporal change in the threshold voltage of the FET. As a result, an incorrect estimation of the chemical properties (e.g. ion activity) of the sample will be determined. This problem is more pronounced for determination of e.g. physiological ion activities or concentrations, where a high accuracy is required (e.g. blood electrolytes monitoring). Therefore, the use of silicon-based CHEMFET's in this kind of applications is very reduced. A further limiting factor for the use of CHEMFET devices is the higher manufacturing cost of these devices. For medical application, one is mostly interested in throw-away devices, which implies very cheap devices. For medical and pharmaceutical applications, devices which can be integrated in plastic materials, are most suitable.

For silicon-based CHEMFET, the integration in plastic material is not straightforward.

In the prior art, thin film transistors based on organic materials have been fabricated. Garnier (Garnier F., Hajlaoui R., Yassar A., Srivastava P., Science, 1994, Vol. 265, p 1684) proposes the use polymeric materials in a thin film transistor. The choice of polymeric materials is determined by the application of the device, i.e. as transistor.

Organic materials, and more especially polymeric materials, have already been used as sensitive parts in combination with a solid-state transducer (inorganic material) or as membranes for immobilization of biomolecules (e.g. enzymes) for specific interactions (G. Harsányi, *Polymer Films in Sensor Applications—Technology, Materials, Devices and Their Characteristics*, TECHNOMIC Publishing Co. Inc. Lancaster-Basel, 1995, p 53–92 and p 149–155; G. Bidan, *Sensors and Actuators B*, Vol 6, 1992, pp. 45–56). In the electroconducting conjugated polymers-based (ECP-based) chemical sensors, there is a direct interaction between the EPC layer and the analyte to detect. The detection mechanism is based on the ion exchange between the ECP layer and the sample. Therefore, a doped ECP layer is needed. A major disadvantage is the required electrochemical deposition of the conducting layer, because this deposition technique is rather difficult to control, which results in the deposition of layers with a lower uniformity and reproducibility. Moreover, the electrochemical deposition of doped conjugated polymeric layers also implies a more complicated, multi-step process. Besides this, due to the electropolymerization reactions, the electroconducting conjugated polymer layer is always p-doped, which means that only anions can be detected. Furthermore, the deposition process requires electrodes made of metallic material or glassy carbon.

SUMMARY OF THE INVENTION

One aim of the invention is to describe an improved device for detecting an analyte in a sample which combines the advantages of existing CHEMFET devices with advantageous properties such as low price, disposability, reduced drift of the device and suitability for biomedical and pharmaceutical applications.

In a first aspect of this invention, a device for detecting an analyte in a sample is provided including an active layer comprising at least a dielectric material, a source electrode and a drain electrode, and a semiconducting layer that provides a current pathway between the source electrode and the drain electrode, wherein the semiconducting layer includes organic-containing semiconducting material and wherein the dielectric material of the active layer is in contact with the semiconducting layer and wherein the active layer is arranged to contact the sample and to influence the conductivity of the semiconducting layer when in contact with the sample containing the analyte. Analyte, as used herein, shall be understood as any chemical molecule, atom or ion comprising but not limited to ions, neutral molecules and biomolecules like enzymes, immunochemicals, hormones and reducible gases. Sample, as used herein, shall be understood as a solid, solution, gas, vapor or a mixture of those comprising at least the analyte. For the purpose of this invention, detecting shall mean determining, identification, measuring of concentrations or activities, measuring a change of concentrations or activities of at least one analyte present in the sample.

In an embodiment of the invention, the active layer includes a dielectric layer.

In an embodiment of this invention, the dielectric layer includes a material with a dielectric constant higher than 3. In order to maximize the current flow between source and drain, the value of the dielectric constant must be as high as possible. Furthermore, a dielectric material with a high value of the dielectric constant will reduce the operational voltage of the device.

The chemically selective dielectric layer can be chosen such that the material of the dielectric layer is essentially inert to the sample. Inert shall, at least for the purpose of this application, means that the capacitance of the dielectric layer without functionalization remains practically constant. Thus, the problems related to the drift of the device can be eliminated. The drift phenomena is typically observed for silicon-based devices, since the silicon layer can be modified when exposed to the sample, resulting in a change of the capacitance of the dielectric layer. This results in slow, temporal change in the threshold voltage, which implies an incorrect estimation of the detection of the analyte.

In an embodiment of the invention, the active layer includes a dielectric layer. The dielectric layer is made of an active material adapted to selectively react with said analyte when said device is exposed to said sample containing said analyte. Depending on the application, the dielectric layer which is exposed to the sample can be modified in such a way that there is an interaction between the analyte and the modified dielectrical material.

In an embodiment of the invention, the dielectric layer includes an organic dielectric material. In a further embodiment of the invention, the dielectric layer includes an inorganic-containing material. The value of the dielectric capacitance is preferably as high as possible. The value of the dielectric constant, $\in$, of the dielectric material is higher than 3, and preferably higher than 5 and preferably higher than 10 and preferably higher than 100.

In a further embodiment of the invention, the active layer can further include a dielectric layer and a membrane layer. Said membrane layer is made of active material and is adapted to selectively react with said analyte when the device is exposed to the sample containing the analyte. Preferably, the chemically sensitive membrane is a conjugated oligomer or a polymer.

In a further aspect of the invention, the organic-containing semiconducting material includes polythiophene (PT), poly (p-phenylene) (PPP), poly(p-phenylene vinylene) (PPV), poly(2,5-thiophene vinylene) (PTV), and polypyrrole (PPy).

In a further embodiment of the first aspect of the invention, the source and drain electrode includes an organic-containing material characterized in that said the surface resistance of the electrodes is lower than 100 $\Omega$/sq. The source and drain electrode can have an interdigitated configuration.

In a further embodiment of this invention, the device can additionally include an encapsulating layer to protect said current pathway between said source electrode and a said drain electrode and a support layer wherein said encapsulating layer and support layer are made of organic-containing material.

In a second aspect of this invention, a system for detecting an analyte in a sample is disclosed, including a device as described in the first aspect of this invention, and a reference field-effect transistor.

In a further aspect of this invention, an array of devices including at least one device as described above is provided.

DETAILED DESCRIPTION OF THE PREFERRED EMBODIMENT

In relation to the appended drawings the present invention is described in detail in the sequel. Several embodiments are disclosed. It is apparent however that a person skilled in the art can imagine several other equivalent embodiments or other ways of practicing the present invention, the spirit and scope thereof being limited only by the terms of the appended claims.

A device for detecting an analyte in a sample, based on organic materials is described. The device can be a chemically sensitive field-effective transistor (CHEMFET). Said device is a thin film transistor in which the gate electrode is missing and which comprises an active layer. Said active layer comprises at least a dielectric layer which is exposed to a sample comprising an analyte to be investigated directly or via a layer with a specific recognition function. Said device can be used for e.g. the detection and measuring of concentrations and activities of chemical species (analyte) present in the sample. Analyte, as used herein, shall be understood as any chemical molecule, atom or ion comprising but not limited to ions, neutral molecules and biomolecules like enzymes, immunochemicals, hormones and reducible gases. Sample, as used herein, shall be understood as a solution, solid, gas, vapor or a mixture of those comprising at least the analyte. For the purpose of this invention, detecting shall mean determining, identification, measuring of concentrations or activities, measuring a change of concentrations or activities of at least one analyte present in the sample. Particularly, said device can be used for the detection of analytes in samples in the biochemical and pharmaceutical field. Furthermore, said device can be used for the detection in samples containing specific analytes e.g. vapors, odor, gases.

In this invention, a device for detecting an analyte in a sample is disclosed, comprising a semiconductor layer, a source electrode, a drain electrode and an active layer. The active layer comprises at least a dielectric material. The semiconducting layer can be chosen such that it acts as current path between source and drain electrode. The electric field in the channel of the device is modified by the interaction of said active layer with an analyte in a sample. The choice of said semiconducting material can be further based on the conductivity of the material, the stability of the material, their availability, their compatibility with standard processing steps as used in the manufacturing of integrated circuits, their deposition characteristics and their cost price.

Said semiconducting layer can be adjacent to the active layer or can not be adjacent to the active layer.

The direct interaction of the semiconducting layer with the analyte is preferably negligible. In this invention, the semiconducting layer comprises an organic-containing semiconducting material. The organic-containing semiconducting material can be used in its neutral (undoped) state and can be a p-type semiconductor or an n-type semiconductor but preferably a p-type semiconductor. Said organic-containing semiconducting material can be an organic polymer e.g. a conjugated polymers. Said conjugated polymer can be but is not limited to Polythiophene (PT), poly(p-phenylene) (PPP), poly(p-phenylene vinylene) (PPV), poly (2,5-thiophene vinylene) (PTV), polypyrrole (PPy) or $C_{60}$-buckminster fullerene. The organic-containing semiconducting layer can also be a conducting oligomer layer wherein said oligomer layer can be but is not limited to α- hexylthiophene (α-6T), pentacene and oligo-phenylene vinylene.

The deposition of the organic-containing semiconducting layer can be done by spin-coating, casting or evaporation of solution processible long-chain polymer or oligomer evaporation. Problems mentioned in the prior-art related to the deposition of electroconducting polymers are avoided by using the above mentioned deposition techniques.

In this invention, a device for detecting an analyte in a sample is disclosed, comprising a semiconductor layer, a source electrode, a drain electrode and an active layer.

Said active layer is chosen such that it assures the field-effect generation and thus the current flowing in the transistor channel. The active layer comprises at least a dielectric material. Preferably, the active layer consists of a dielectric layer or a dielectric layer covered with an analyte-specific membrane. In order to maximize the current flowing between source and drain, the dielectric capacitance is preferably as high as possible. This can be achieved by depositing the dielectric material in very thin layers and by using materials with a high dielectric constant. The thickness of the layers is typically from $0.1\mu$ up to $0.5\mu$. The dielectric constant, $\in$, of the dielectric material is higher than 3, and preferably higher than 5 and preferably higher than 10 and preferably higher than 100. The water absorption of the active layer is preferably as low as possible and preferably negligible.

The drift of the device, as mentioned in the background of the invention can be avoided or at least reduced by using a dielectric layer which is inert to the sample. Inert shall, at least for the purpose of this application, mean that the capacitance of the dielectric layer without functionalization remains practically constant. Moreover, taking into account that organic-containing semiconducting materials have a large density of trapping levels in the band gap, a dielectric material with a high $\in$ value will reduce the operational voltage. This is a significant advantage compared to the prior art for devices with a specific sensing function such as the CHEMFET devices.

The dielectric layer can be chosen such that it has a specific sensitivity towards the chemical species which must be detected or measured. The dielectric layer can comprise an organic-containing dielectric material or an inorganic-containing dielectric material.

When the dielectric layer comprises an organic-containing material and in order to achieve the specific chemical sensitivity, the surface of the dielectric layer must be functionalized. functionalization means that the chemical properties of the dielectric material in contact with the sample are modified in such a way that there is an interaction between the analyte and the modified dielectrical material. The functionalization depends on the nature of the analyte to detect. The analyte which has to be detected can be, but is not limited to an ion, an organic biomolecule or metabolic biomolecules. When the analyte is an ion, ion-selective groups are synthesized on e.g. a polymer or an oligomer. For the detection of ions like $Na^+$, $K^+$, $Ca^{2+}$, $Mg^{2+}$, $Cl^-$ or any other ion, the ion-selective groups can be selected from the group comprising e.g. a crown-ether, a cryptand, or any other ion-complex forming chemical group. Organic biomolecules can be detected via e.g. an enzymatic reaction, that leads to a change in e.g. the pH. This pH change will be used for the detection and measuring of the enzymatic reaction. The same principle is used for monitoring the cellular metabolism when the enzymatic layer is replaced by a layer of cells. Also, the recognition molecule can be entrapped in a matrix of the dielectric material.

The dielectric material can also comprise an inorganic-containing material. Said inorganic-containing material can comprise an inorganic oxide, an inorganic nitride or an inorganic oxynitride. Said inorganic-containing material can comprise an amorphous metallic material selected from the group comprising $TiO_2$, $BaTiO_3$, $Ba_xSr_{1-x}TiO_3$, $Pb(Zr_xT_{1-x})O_3$, $Ta_2O_5$, $SrTiO_3$, $BaZrO_3$, $PbTiO_3$, $LiTaO_3$ etc. When the inorganic-containing material has a specific recognition function towards the analyte, the dielectric layer is exposed directly to the analyte. For e.g. an inorganic oxide, protons or concentrations of protons can be detected or measured by direct exposure of the dielectric layer to the sample containing the analyte.

The organic or inorganic-containing dielectric layer can also show no specific recognition function towards the analyte. Therefore, an analyte-specific membrane is deposited on the dielectric layer. The membrane layer is made of an active material. The analyte specific membrane can be a polymeric matrix which contains the specific recognition molecule. Possible polymeric materials and specific recognition molecules are given in G. Harsányi, *Polymer Films in Sensor Applications—Technology, Materials, Devices and Their Characteristics*, TECHNOMIC Publishing Co. Inc. Lancaster-Basel, 1995, pp.2. and W. Gopel, J. Hesse, J. N. Zemel, *Sensors: A Comprehensive Survey*, Vol.2, Part.I, 1991, pp.467–528. The analyte specific membrane can be but is not limited to a PVC matrix, polysiloxane-based membranes and Langmuir-Blodgett films. Said specific recognition molecule can be, but is not limited to valinomycin for $K^+$ detection, specific enzymes for detecting organic inactive species (glucose, cholesterol).

In this invention, a device for detecting an analyte in a sample is disclosed, comprising a source electrode, a drain electrode, a semiconductor layer and an active layer.

Figure 3:
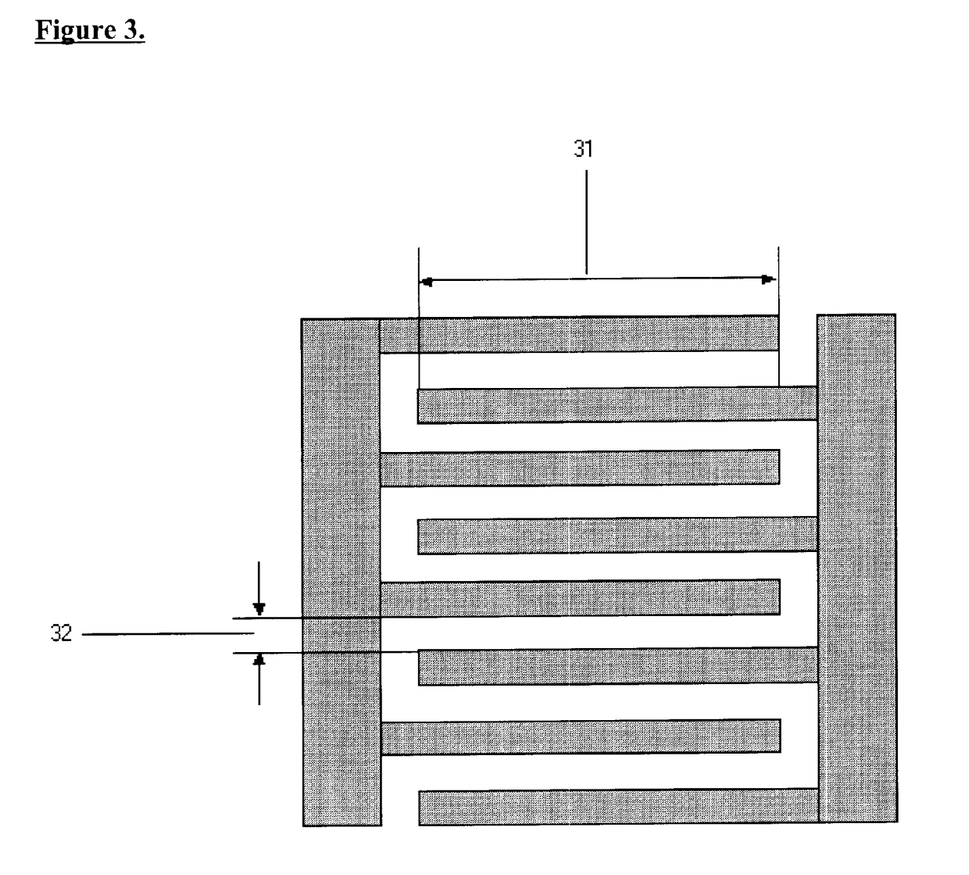
FIG. 3 illustrates an interdigitated source-drain electrodes configuration.

The source electrode and the drain electrode can be made of an organic-containing material. The organic-containing material can be chosen such that the conductivity of the material is in the metallic range. The surface resistance of the electrodes is preferably lower than 100 Ω/sq. Electrodes made of organic-containing material are preferred because this results in an optimal quality of the contact between the electrodes and the organic-containing semiconducting layer. Said organic-containing material can be a polymer or an oligomer. The polymer can be but is not limited to polyaniline doped with camphor sulfonic acid. The source and drain electrode can also be made of a metal like gold, platinum or aluminum, depending on the HOMO and LUMO energy levels in the organic semiconductor. The source and drain electrodes are preferably patterned lithographically. The source and drain electrodes can have an interdigitated configuration, as it is illustrated in FIG. 3, in order to achieve maximum electric current flowing into the transistor channel. The channel width 31-to-length 32 ratio, and the number of fingers must be optimized in order to achieve the desired level for the output current. This configuration is preferred because of the low conductivity of the organic-containing semiconductor material.

In a further embodiment of the present invention, said device further comprises a support layer. The support layer is chosen such that it assures the deposition of the active layers and that it maintains the flatness of the device. The support can be made of polymeric material with a high chemical resistance and thermal properties which are determined by the further deposition steps. The upper working temperature of said support layer is higher then 100° C., preferably higher than 150° C., and preferably higher than 300° C. Such materials can be polyvinyldifluoride, high density polyethylene, polyimide, polytetrafluoroethylene (Teflon™), polypropylene or any other material which fulfills the above mentioned properties.

Furthermore, the device can be encapsulated by an encapsulating layer. The semiconducting layer and the electrodes are encapsulated such that the current pathway between source and drain electrode in the semiconducting layer is protected from the air and from the sample. The encapsulating layer can be made, but is not limited to an epoxy resin (such as EP42HT, purchased from Master Bond Inc.) or parylene.

Figure 2:
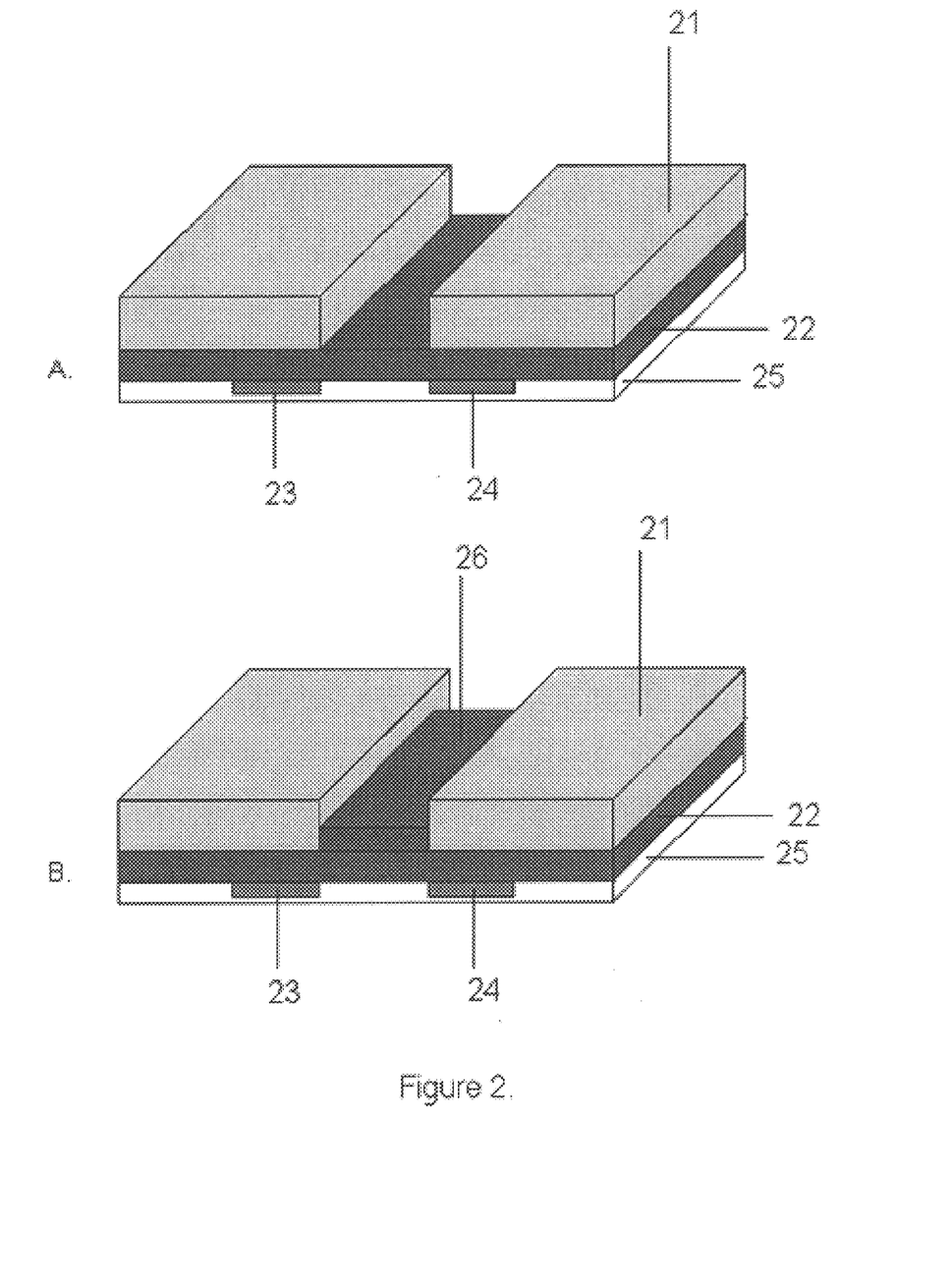
FIGS. 2A and 2B illustrate a configuration of a CHEMFET device according to the present invention.

An embodiment of the invention is given in FIG. 2B.

FIG. 2B represents a device for detecting an analyte in a sample according to the present invention. Said device can be a chemical selective field-effect transistor. Besides the structure of the CHEMFET, a method is disclosed which can be used for the manufacturing of a single sensor or an array of sensors. Such sensor array has a multitude of sensing sites, each sensing site being a sensor. In a preferred embodiment, the inert support layer is a common support layer of the array.

A support substrate 21 selected according to the further processing steps as known in the integrated circuit manufacturing. In a next step, a dielectric layer 22 deposited on the support layer. The dielectric material is an inorganic oxide and can be selected from the inorganic oxides mentioned above. The dielectric layer is deposited by RF sputtering at a temperature range from 5° C. to 50° C. and preferably at room temperature. The thickness of the dielectric layer is preferably about 0.1μ. In a next step, the source and drain electrode are deposited. First, a layer of an organic-containing material, e.g. doped polyaniline with camphorsulfonic acid, is deposited on the dielectric layer. Subsequently, the layer will be patterned lithographically such that the source electrode 23 and the drain electrode 24 are formed. Then, the organic-containing semiconducting layer 25 is deposited on both electrodes and on the remaining dielectric layer. The semiconducting layer has preferably a thickness between 0.1 and 0.5 μm and is deposited by spin-coating. An encapsulating layer is formed such that the source and drain electrodes and the semiconducting layer are protected from air and from the sample. In a last step, an analyte specific membrane 26 is deposited on the dielectric layer and adjacent to holes formed in the support layer. The composition of the membrane depends on the nature of the analyte to detect.

Since organic-containing materials is are involved in the most processing steps, the temperature range for all processing steps is as low as possible and preferably lower than 300° C.

In a further embodiment of this invention, a structure as represented in FIG. 2A is disclosed.

The device as described can be used with or without a reference electrode. A reference electrode or a reference FET can be used, depending on the measurement method. For instance, in the fixed gate voltage mode, the chemical environment (e.g. aqueous solution) is kept at a fixed potential in respect to the sensor source electrode, and the electric current flowing between source and drain electrodes is recorded in function of the changes in the chemical environment of the sensor. This is realized by adjusting the voltage drop between the source electrode (which is usually grounded) and a reference electrode or reference FET. Also, in the constant drain current mode, the current between source and drain is kept constant by adjusting the voltage drop $V_{GS}$ between the reference electrode or reference FET and the source electrode. The response of the sensor is the variation of this voltage drop, $V_{GS}$, in function of the changes in the chemical environment.

Figure 4:
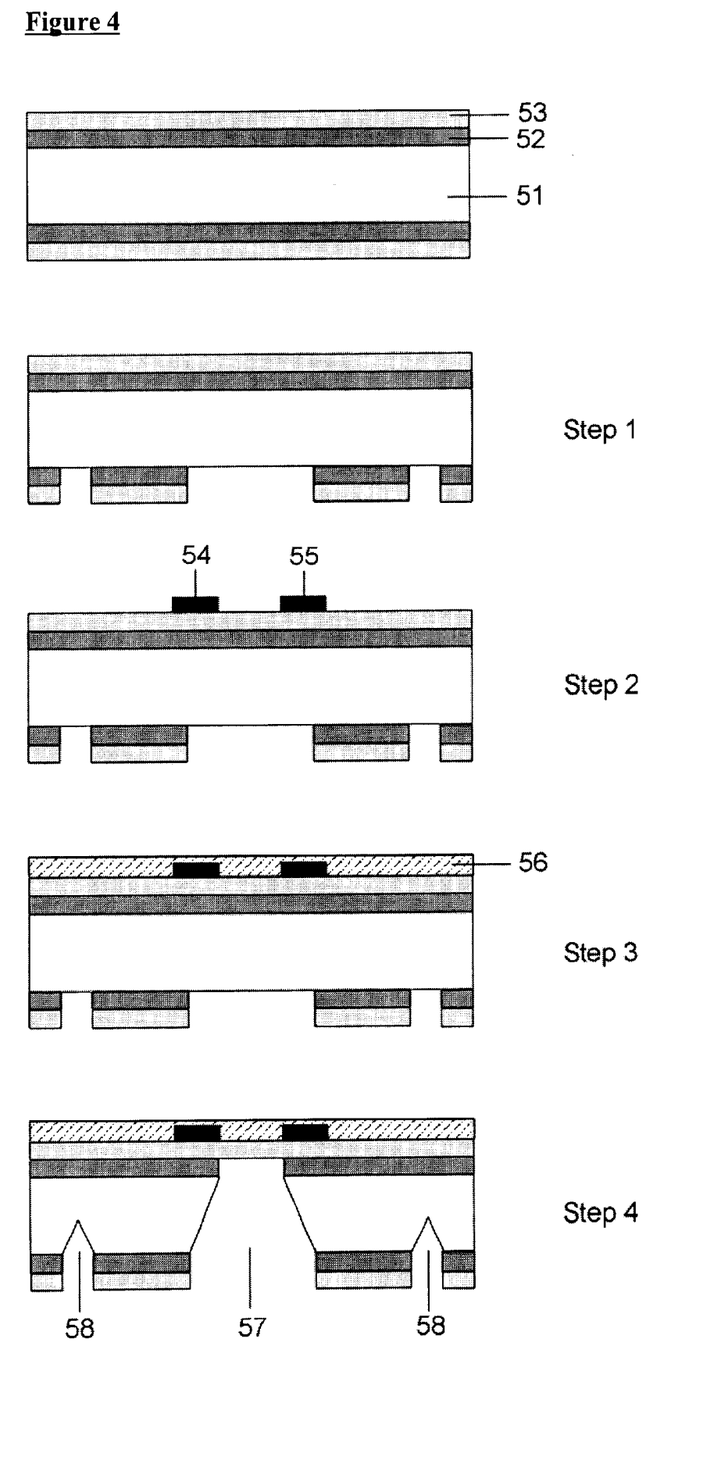
FIG. 4 illustrates the process flow and device configuration according to the preferred embodiment of the present invention.

In the preferred embodiment, a device as depicted in FIG. 4 is disclosed.

The silicon wafer 51 with a thickness of 650 μm is used as a support for device. This is only a mechanical support structure and does not perform an active role in the device operation. Two layers of silicon oxide (470 nm) 53 and silicon nitride (150 nm) 52, respectively, have been deposited on the both side of the silicon wafer, as can be seen from the FIG. 4. The thickness of these two layers has been chosen to reduce the mechanical stress in the membrane. The silicon oxide layer has the function of reducing the mechanical stress. The silicon nitride layer performs a double role in this case: it represents the active layer (being a dielectric sensitive gate) and, at the same time, it is a stopping layer for the anisotropic KOH etching.

The processing steps are illustrated in FIG. 4. First a mask was patterned, by means of conventional lithography and dry etching, in the back side oxide and nitride layers to define the active area 57 and the "V" grooves 58 that are used for easy cleavage (see FIG. 4—Step 1). Subsequently, the gold source 54 and drain 55 interdigitated electrodes with a thickness of 100 nm were deposited by thermal evaporation and patterned by lift-off technique (FIG. 4—Step 2). In the next step, the P3HT (poly-3-hexyl thiophene) semiconducting layer 56 was spin-coated onto the electrodes from a chloroform solution with a concentration of 0.8% weight (FIG. 4 Step 3). The window defining the sensitive area was made by etching completely the silicon in KOH 35% weight solution in water at 40° C. (FIG. 4—Step 4). This delimitates an active area of 1 mm×1 mm on the silicon nitride surface.

After cleavage, the resulting device was wire-bonded on a thick-film alumina substrate and encapsulated with EP42HT, a two-component epoxy that cures at room temperature, purchased from Master Bond Inc.

What is claimed is:

1. A device for detecting an analyte in a sample comprising:
   an active layer comprising a dielectric material, wherein said dielectric material is an inorganic containing material with a dielectric constant higher than 10;
   a source electrode and a drain electrode; and
   a semiconducting layer for providing a current pathway between said source electrode and said drain electrode, wherein said semiconducting layer consists essentially of an organic containing semiconducting material, wherein said dielectric material of said active layer is substantially in contact with said semiconducting layer, and wherein said active layer is arranged to contact said sample and to influence the conductance of said semiconducting layer when in contact with said sample containing said analyte.

2. A device as recited in claim 1 wherein said active layer consists essentially of a dielectric layer.

3. A device as recited in claim 1 wherein said dielectric material comprises an amorphous metallic material selected from the group consisting of $TiO_2$, $BaTiO_3$, $Ba_xSr_{1-x}TiO_3$, $Pb(Zr_xT_{1-x})O_3$, $Ta_2O_5$, $SrTiO_3$, $BaZrO_3$, $PbTiO_3$, $LiTaO_3$, and $Ta_2O_5$.

4. A device as recited in claim 1 wherein said active layer comprises a dielectric layer.

5. A device as recited in claim 4 wherein said active layer consists essentially of a dielectric layer.

6. A device as recited in claim 4 wherein said dielectric layer comprises an active material arranged to selectively react with said analyte when said device is exposed to said sample containing said analyte.

7. A device as recited in claim 1 wherein said active layer consists essentially of said dielectric layer and a membrane layer.

8. A device as recited in claim 7 wherein said membrane layer comprises an active material arranged to selectively react with said analyte when said device is exposed to said sample containing said analyte.

9. A device as recited in claim 1 wherein said organic containing semiconducting material comprises a conjugated oligomer or conjugated polymer.

10. A device as recited in claim 9 wherein said organic containing semiconducting material is selected from the group consisting of polythiophene, poly(p-phenylene), poly (p-phenylene vinylene), poly(2,5-thiophene vinylene), polypyrrole, and mixtures thereof.

11. A device as recited in claim 1 wherein said source electrode and said drain electrode comprise an organic containing material wherein a surface resistance of said source electrode and said drain electrode is lower than 100 Ω/sq.

12. A device as recited in claim 1 herein said source electrode and said drain electrode have an interdigitated configuration.

13. A device as recited in claim 1 further comprising:
   an encapsulating layer to protect said current pathway between said source electrode and said drain electrode; and
   a support layer, wherein said encapsulating layer and said support layer are made of an organic containing material.

14. A system for detecting an analyte in a sample, the system comprising a device as recited in claim 1 and a reference field-effect transistor.

15. An array of devices, said array comprising at least one device as recited in claim 1.

16. A device for detecting an analyte in a sample, the device comprising:
   an active layer comprising a dielectric material, wherein said dielectric material is an organic containing material;
   a source electrode and a drain electrode; and
   a semiconducting layer for providing a current pathway between said source electrode and said drain electrode, wherein said semiconducting layer consists essentially of an organic containing semiconducting material, wherein said dielectric material of said active layer is substantially in contact with said semiconducting layer, and wherein said active layer is arranged to contact said sample and to influence the conductance of said semiconducting layer when in contact with said sample containing said analyte.

17. A device as recited in claim 16 wherein said active layer consists essentially of a dielectric layer.

18. A device as recited in claim 16 wherein said dielectric layer comprises an active material arranged to selectively react with said analyte when said device is exposed to said sample containing said analyte.

19. A device as recited in claim 16 wherein said active layer consists essentially of said dielectric layer and a membrane layer.

20. A device as recited in claim 19 wherein said membrane layer comprises an active material arranged to selectively react with said analyte when said device is exposed to said sample containing said analyte.

21. A device as recited in claim 16 wherein said organic containing semiconducting material comprises a conjugated oligomer or conjugated polymer.

22. A device as recited in claim 21 wherein said organic containing semiconducting material is selected from the group consisting of polythiophene, poly(p-phenylene), poly(p-phenylene vinylene), poly(2,5-thiophene vinylene), polypyrrole, and mixtures thereof.

23. A device as recited in claim 16 wherein said source electrode and said drain electrode comprise an organic containing material wherein a surface resistance of said source electrode and said drain electrode is lower than 100 Ω/sq.

24. A device as recited in claim 23 wherein said source electrode and said drain electrode have an interdigitated configuration.

25. A device as recited in claim 16 further comprising:
an encapsulating layer to protect said current pathway between said source electrode and said drain electrode; and
a support layer, wherein said encapsulating layer and support layer comprise an organic containing material.

26. A system for detecting an analyte in a sample, the system comprising a device as recited in claim 16 and a reference field-effect transistor.

27. An array of devices, said array comprising at least one device as recited in claim 16.

* * * * *